United States Patent
Robinson et al.

(10) Patent No.: US 10,568,869 B2
(45) Date of Patent: Feb. 25, 2020

(54) METHODS FOR DIAGNOSING AND TREATING PROSTATE CANCER

(71) Applicant: Cornell University, Ithaca, NY (US)

(72) Inventors: Brian Robinson, New York, NY (US); Jonathan Zippin, New York, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 398 days.

(21) Appl. No.: 14/650,193

(22) PCT Filed: Dec. 11, 2013

(86) PCT No.: PCT/US2013/074337
§ 371 (c)(1),
(2) Date: Jun. 5, 2015

(87) PCT Pub. No.: WO2014/093460
PCT Pub. Date: Jun. 19, 2014

(65) Prior Publication Data
US 2015/0313878 A1   Nov. 5, 2015

Related U.S. Application Data

(60) Provisional application No. 61/735,856, filed on Dec. 11, 2012.

(51) Int. Cl.
*A61K 31/4184* (2006.01)
*C12N 15/113* (2010.01)
*G01N 33/574* (2006.01)

(52) U.S. Cl.
CPC ...... *A61K 31/4184* (2013.01); *C12N 15/1137* (2013.01); *G01N 33/57434* (2013.01); *C12N 2310/14* (2013.01); *C12N 2310/531* (2013.01); *C12N 2320/30* (2013.01); *G01N 2333/988* (2013.01)

(58) Field of Classification Search
CPC ............ A61K 31/4184; A61K 31/7105; A61K 31/713; C12N 15/1137; C12N 2310/14; C12N 2310/531; C12N 2320/30; C12Y 406/01001; G01N 2333/988; G01N 33/57434
See application file for complete search history.

(56) References Cited

U.S. PATENT DOCUMENTS

| | | | |
|---|---|---|---|
| 4,946,778 A | 8/1990 | Ladner et al. | |
| 5,132,405 A | 7/1992 | Huston et al. | |
| 5,225,539 A | 7/1993 | Winter | |
| 5,476,786 A | 12/1995 | Huston | |
| 5,585,089 A | 12/1996 | Queen et al. | |
| 5,693,761 A | 12/1997 | Queen et al. | |
| 5,693,762 A | 12/1997 | Queen et al. | |
| 6,544,768 B1 | 4/2003 | Buck et al. | |
| 9,649,295 B2 * | 5/2017 | Buck | A61K 31/415 |
| 2007/0244174 A1* | 10/2007 | Buck | A61K 31/415 514/395 |
| 2009/0275047 A1 | 11/2009 | Saalau-Bethell | |
| 2011/0305640 A1 | 12/2011 | Buck et al. | |
| 2012/0150032 A1 | 6/2012 | Gudmundsson et al. | |
| 2013/0065246 A1 | 3/2013 | Magro et al. | |

FOREIGN PATENT DOCUMENTS

| | | |
|---|---|---|
| WO | 2004/029616 A2 | 4/2004 |
| WO | WO 2001/085753 A1 | 11/2011 |

OTHER PUBLICATIONS

Flacke et al., The role of soluble adenylyl cyclase in proliferation and apoptosis of prostate cancer, 2010, Onkologie, vol. 33, No. 6, p. 86, abstract No. V289.*
S. H. Woolf, "Screening for Prostate Cancer With Prostate-Specific Antigen", 1995, The New England Journal of Medicine, 33(21), pp. 1401-1405 (Year: 1995).*
Gu et al., "Prostate stem cell antigen (PSCA) expression increases with high gleason score, advanced stage and bone metastasis in prostate cancer", 2000, Oncogene, 19(10), pp. 1288-1296 (doi.org/10.1038/sj.onc.1203426). (Year: 2000).*
Flacke et al., "Type 10 Soluble Adenylyl Cyclase Is Overexpressed in Prostate Carcinoma and Controls Proliferation of Prostate Cancer Cells", 2013, J. Biol. Chem., 288(5), pp. 3126-3135 (doi: 10.1074/jbc.M112.403279 originally published online Dec. 19, 2012) (Year: 2013).*
Barnes et al., Immunohistochemical determination of oestrogen receptor: comparison of different methods of assessment of staining and correlation with clinical outcome of breast cancer patients, *British Journal of Cancer*, 74: 1445-51 (1996).
Brummelkamp et al., A System for Stable Expression of Short Interfering RNAs in Mammalian Cells, *Science*, 296: 550-553 (2002).
Buck et al., Cytosolic adenylyl cyclase defines a unique signaling molecule in mammals, *Proc. Natl. Acad. Sci. USA*, 96: 79-84 (1999).
Castanotto et al., Functional siRNA expression from transfected PCR products, *RNA*, 8: 1454-1460 (2002).
Cole et al., The EBV-hybridoma technique and its application to human lung cancer, *Monoclonal Antibodies and Cancer Therapy*, Alan R. Liss, Inc., pp. 77-96 (1985).
Cote et al., Generation of human monoclonal antibodies reactive with cellular antigens, *Proc. Nati. Acad. Sci. USA*, 80: 2026-2030 (1983).
Dharmacon, Lafayette, CO; Catalogue No. L-006353-00.
Dharmacon, Lafayette, CO; Catalogue No. D-001810-1.
Dumont et al., The cyclic AMP-mediated stimulation of cell proliferation, *TIBS Trends in Biochemical Sciences*, 14: 67-71 (1989).

(Continued)

*Primary Examiner* — My-Chau T. Tran
(74) *Attorney, Agent, or Firm* — Leydig, Voit & Mayer, Ltd.

(57) ABSTRACT

The invention is directed to a method of inhibiting prostate cancer cell proliferation using a substance that inhibits the activity of a soluble adenylyl cyclase (sAC) protein. The invention also is directed to methods of diagnosing and prognosticating prostate cancer in a subject by evaluating sAC gene or protein expression in the subject.

6 Claims, 5 Drawing Sheets
Specification includes a Sequence Listing.

(56) References Cited

OTHER PUBLICATIONS

Edge et al., The American Joint Committee on Cancer: the 7th Edition of the *AJCC Cancer Staging Manual* and the Future of TNM, *Annals of Surgical Oncology*, 17: 1471-1474 (2010).
SEER Program Coding and Staging Manual, NIH Publication No. 13-5581, U.S. Department of Health and Human Services National Institutes of Health National Cancer Institute (2013).
Farrell et al., Somatic 'Soluble' Adenylyl Cyclase Isoforms Are Unaffected in $Sacy^{tm1Lex}/Sacy^{tm1Lex}$ 'Knockout' Mice, *PLoS ONE*, 3(9): 1-9 (2008).
Grossfeld et al., Prostate Cancer Early Detection: a Clinical Perspective, *Epidemiologic Reviews*, 23(1): 173-180 (2001).
Hess et al., The "Soluble" Adenylyl Cyclase in Sperm Mediates Multiple Signaling Events Required for Fertilization, *Dev. Cell.*, 9(2): 249-259 (2005).
Hewer et al., PKA and Epac synergistically inhibit smooth muscle cell proliferation,*Journal of Molecular and Cellular Cardiology*, 50(1): 87-98 (2011).
Hochbaum et al., Epac, in Synergy with cAMP-dependent Protein Kinase (PKA), Is Required for cAMP-mediated Mitogenesis, *The Journal of Biological Chemistry*, 283(8): 4464-4468 (2008).
Horwich, Systemic treatment for prostate cancer, *Annals of Oncology*, 17 (Supplement 10): x211-213 (2006).
Huang et al., Efficient and specific gene knockdown by small interfering RNAs produced in bacteria, *Nat. Biotechnol.*, 31(4): 350-356 (2013).
Humphrey et al., Prospective Characterization of Pathological Features of Prostatic Carcinomas Detected Via Serum Prostate Specific Antigen Based Screening, *The Journal of Urology*, 155: 816-820 (1996).
Jaiswal et al., Identification and Functional Analysis of Splice Variants of the Germ Cell Soluble Adenylyl Cyclase, *The Journal of Biological Chemistry.*, 276(34): 31698-31708 (2001).
Kamenetsky, Mammalian Cells Possess Multiple, Distinctly Regulated cAMP Signaling Cascades, Ph.D. Dissertation, Weill Medical College of Cornell University, Publication No. AAT 3251733 [ProQuest Document ID 1276395511] (2006).
Kohler et al., Continuous cultures of fused cells secreting antibody of predefined specificity, *Nature*, 256: 495-497 (1975).
Kozbor et al., The production of monoclonal antibodies from human lymphocytes, *Immunology Today*, 4(3): 72-79 (1983).
Lee et al., Expression of small interfering RNAs targeted against HIV-1 rev transcripts in human cells, *Nature Biotechnology*, 19: 500-505 (2002).
Leone et al., $PGE_2$ inhibits apoptosis in human adenocarcinoma Caco-2 cell line through $RasPI_3K$ association and cAMP-dependent kinase A activation, *American Journal of Physiology, Gastrointestinal and Liver Physiology*, 293(4): G673-G681 (2007).
Li et al., DNA methylation in prostate cancer, *Biochimica et Biophysica Acta*, 1704: 87-102 (2004).
Lucchi, et al., 8-Chloro-Cyclic AMP and Protein Kinase A I-Selective Cyclic AMP Analogs Inhibit Cancer Cell Growth through Different Mechanisms, *PLoS One*, 6(6): e20785 (2011).
Magro et al., Soluble Adenylyl Cyclase Antibody Profile as a Diagnostic Adjunct in the Assessment of Pigmented Lesions, *Arch. Dermatol.*, 148(3): 335-344 (2012).
Mettlin et al., The National Cancer Data Base Report on Prostate Carcinoma after the Peak in Incidence Rates in the U. S., *Cancer*, 83(8): 1679-1684 (1998).
Mettlin et al., Why Is the Prostate Cancer Death Rate Declining in the United States?, *Cancer*, 82(2): 249-251 (1998).
Misra et al., Epac1-Induced Cellular Proliferation in Prostate Cancer Cells Is Mediated by B-Raf/ERK and mTOR Signaling Cascades, *Journal of Cellular Biochemistry*, 108: 998-1011 (2009).
Morrison et al., Isolation of Transformation-Deficient *Streptococcus pneumonia* Mutants Defective in Control of Competence, Using Insertion-Duplication Mutagenesis with the Erythromycin Resistance Determinant of pAMβ, *Journal of Bacteriology*, 159: 870-876 (1984).
Neuberger et al., Recombinant antibodies possessing novel effector functions, *Nature*, 312: 604-608 (1984).
Paul et al., Effective expression of small interfering RNA in human cells , *Nature Biotechnology*, 20: 505-508 (2002).
Postma, Treatment of prostate cancer, *Annals of Oncology*, 17(Supplement 10): x207-210 (2006).
Remington, *The Science and Practice of Pharmacy*, 21st Edition, Lippincott Williams & Wilkins, Philadelphia, PA (2001).
Rinne et al., Gene silencing in adult rat cardiac myocytes in vitro by adenovirus-mediated RNA interference, *J. Muscle Res. Cell. Motil.*, 27: 413-421 (2006).
Rozengurt, Early signals in the mitogenic response, *Science*, 234: 161-168 (1986).
Rudolph et al., Cyclic AMP Activation of the Extracellular Signal-regulated Kinases 1 and 2, *Journal of Biological Chemistry*, 279(15): 14828-14834 (2004).
Sambrook et al., *Molecular Cloning: A Laboratory Manual*, 4th edition., Cold Spring Harbor Press, Cold Spring Harbor, N.Y. (2012).
Seyhan et al., Complete, gene-specific siRNA libraries: Production and expression in mammalian cells, *RNA*, 11(5): 837-846 (2005).
Smith et al., The phosphodiesterase PDE4B limits cAMP-associated PI3K/AKT—dependent apoptosis in diffuse large B-cell lymphoma, *Blood Journal*, 105(1): 308-316 (2005).
Sui et al., A DNA vector-based RNAi technology to suppress gene expression in mammalian cells, *Proc. Natl. Acad. Sci. USA*, 99(8): 5515-5520 (2002).
Takeda et al., Construction of chimaeric processed immunoglobin genes containing mouse variable and human constant region sequences, *Nature*, 314: 452-454 (1985).
Thompson et al., *The New England Journal of Medicine*, 350(22): 2239-2246 (2004).
Velculescu et al., Serial Analysis of Gene Expression, *Science*, 270: 484-487 (1995).
Wu et al., Soluble adenylyl cyclase is required for netrin-1 signaling in nerve growth cones, *Nat. Neurosci.*, 9(10): 1257-1264 (2006).
Yu et al., An Integrated Network of Androgen Receptor, Polycomb, and TMPRSS2-ERG Gene Fusions in Prostate Cancer Progression, *Cancer Cell*, 17(5): 443-454 (2010).
Zhang et al., The Pro-apoptotic Protein Bim Is a Convergence Point for cAMP/Protein Kinase A- and Glucocorticoid-promoted Apoptosis of Lymphoid Cells, *The Journal of Biological Chemistry*, 279(20): 20858-20865 (2004).
Zhou et al., Expression and Diagnostic Utility of Alpha-Methylacyl-CoA-Racemase (P504S) in Foamy Gland and Pseudohyperplastic Prostate Cancer, *The American Journal of Surgical Pathology*, 27(6): 772-778 (2003).
Zippin et al., Compartmentalization of bicarbonate-sensitive adenylyl cyclase in distinct signaling microdomains, *FASEB Journal*, 17(1): 82-84 (2003).
Zippin et al., Soluble Adenylyl Cyclase Defines a Nuclear cAMP Microdomain in Keratinocyte Hyperproliferative Skin Diseases, *J. Invest. Dermatol.*, 130(5): 1279-1287 (2010).
GenBank Accession Record No. NM_021684.1, submitted on Aug. 10, 2014.
GenBank Accession Record No. NM_001167749, submitted on Mar. 24, 2014.
Flacke et al., "Type 10 Soluble Adenylyl Cyclase Is Overexpressed in Prostate Carcinoma and Controls Proliferation of Prostate Cancer Cells", *Journal of Biological Chemistry*, 288(5):3126-3135 (2012).
U.S. Patent & Trademark Office, International Search Report in Application No. PCT/US2013/074337 (dated Mar. 18, 2014).
European Patent Office, Extended European Search Report in Application No. 13862640.3 (dated May 3, 2016).

\* cited by examiner

Knockdown-Detection

B

Proliferation

C

Cytotoxicity

D

Apoptosis

METHODS FOR DIAGNOSING AND TREATING PROSTATE CANCER

CROSS-REFERENCE TO RELATED APPLICATIONS

This patent application claims the benefit of U.S. Provisional Patent Application No. 61/735,856, filed Dec. 11, 2012, which is incorporated by reference.

STATEMENT REGARDING FEDERALLY SPONSORED RESEARCH AND DEVELOPMENT

This invention was made with Government support under Grant Number CA160657 awarded by the National Institutes of Health. The Government has certain rights in the invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 4,273 Byte ASCII (Text) file named "720997_ST25.TXT," created on Jun. 5, 2015.

BACKGROUND OF THE INVENTION

Prostate cancer is the most common malignancy and the second leading cause of death among men in the U.S. (Li et al., *Biochim. Biophys. Acta*, 1704: 87-102 (2004)). The National Cancer Institute (NCI) estimates that in 2013, over 230,000 new cases of prostate cancer will be diagnosed, and over 29,000 men will die of prostate cancer in the United States. The prostate-specific antigen or PSA test continues to be widely used in the early detection of prostate cancer. While the PSA test has resulted in the majority of prostate cancer cases being diagnosed in asymptomatic men (Mettlin et al., *Cancer*, 83(8): 1679-1684 (1998a); Mettlin et al., *Cancer*, 82(2): 249-251 (1998b); Humphrey et al., *J. Urol.*, 155: 816-820 (1996); and Grossfeld et al., *Epidemiol. Rev.*, 23(1): 173-180 (2001)), the PSA test suffers from poor specificity, which can be as low as 33% when a PSA cut-off level of 2.6 ng/mL is used (Thompson et al., *N. Engl. J. Med.*, 350: 2239-2246 (2004)), even though the sensitivity can be as high as 83%. The poor specificity of the PSA test is a direct result of increased secretion of PSA in other diseases of the prostate, such as benign prostate hyperplasia (BPH) and prostatitis. Thus, an elevated PSA level indicates the need for additional screening typically in the form of needle biopsy. Ultimately, the results of needle biopsies lead to the diagnoses of prostate cancer. Over 1 million needle biopsies of prostates are performed each year at a cost of about $1,500 each and much discomfort to the patient. However, less than 200,000 of these result in a diagnosis of prostate cancer. Therefore, the majority of needle biopsies are being performed needlessly.

Currently, several diagnostic markers are used clinically to distinguish benign prostate tissue from malignant prostate tissue, including, for example, alpha-methylacyl-CoA racemase (AMACR, p504s) (Zhou et al., *Amer. J. Surgical Pathology*, 27(6): 772-778 (2003)) and the TMPRSS2-ERG fusion gene (Yu et al., *Cancer Cell*, 17(5): 443-54 (2010)). These markers, however, lack the specificity needed for consistently reliable diagnoses. Similarly, prognostic biomarkers such as the TMPRSS2-ERG gene fusion, PTEN deletion, and SPINK1 overexpression also lack the specificity to assess a wide range of prostate cancers, leaving a significant number of prostate cancers without further prognostic information apart from calculating a cancer's Gleason score. Currently there are no known biomarkers that can indicate prostate cancers that have invaded into the periprostatic soft tissue.

Thus, there is a need for non-invasive methods of diagnosing and prognosticating prostate cancer, as well as improved methods for treating prostate cancer. The invention provides such methods.

BRIEF SUMMARY OF THE INVENTION

The invention provides a method of inhibiting proliferation of prostate cancer cells, which comprises contacting prostate cancer cells with a substance that inhibits that activity of a soluble adenylyl cyclase (sAC) protein, whereupon proliferation of the prostate cancer cells is inhibited.

The invention also provides a method for diagnosing prostate cancer in a male subject. The method comprises (a) obtaining a sample of cells from the prostate of a male subject, (b) assaying the sample for expression of the sAC gene or production of the sAC protein, and (c) comparing the level of sAC gene expression or sAC protein production in the sample to a control, wherein overexpression of sAC gene or protein in the sample as compared to the control is indicative of prostate cancer in the male subject.

The invention provides a method for selecting a treatment option for a prostate cancer subject. The method comprises (a) obtaining a sample of prostate cancer cells from a prostate cancer subject, (b) assaying the sample for expression of the sAC gene or production of the sAC protein, (c) comparing the level of sAC gene or protein expression in the sample to a control, (d) prognosticating the prostate cancer in the subject based on the comparison performed in (c), (e) selecting a treatment option for the subject based on the subject's prognosis in (d), and (f) providing the treatment option to the subject.

BRIEF DESCRIPTION OF THE SEVERAL VIEWS OF THE DRAWINGS

FIGS. 4A-4F are graphs and images which illustrate experimental data depicting that inhibition or knockdown of sAC induces cell cycle arrest at the $G_2$ phase.

FIGS. 5A-5E are graphs and images which illustrate experimental data depicting that sAC controls proliferation and the cell cycle in a PKA-independent and EPAC-dependent manner.

DETAILED DESCRIPTION OF THE INVENTION

The invention provides methods for inhibiting proliferation of prostate cancer cells, diagnosing prostate cancer, and selecting treatment options for prostate cancer patients based on the expression of the soluble adenylyl cyclase (sAC) protein. sAC is a soluble signaling enzyme involved in the production of cyclic AMP (cAMP) (see, e.g., International Patent Application Publication WO 2001/085753 and U.S. Pat. No. 6,544,768). The expression of sAC has been observed in keratinocytes, melanocytes, mononuclear cells, eccrine ducts, and nerves of human skin (Zippin et al., *J. Invest. Dermatol.*, 130: 1279-1287 (2010)), as well as other regions of the body. cAMP mediates cellular responses to nutritional conditions and extracellular signals and has long been known to exert both stimulatory and inhibitory effects on cell growth and proliferation (Dumont et al., *Trends Biochem. Sci.*, 14: 67-71 (1989); and Rozengurt et al., *Science*, 234: 161-166 (1986)).

cAMP-dependent signaling has been shown to play a role in several signaling pathways that control cell proliferation and apoptosis; however, the specific effects of cAMP signaling on proliferation and apoptosis are not well established. For example, elevation of cellular cAMP content by stimulation of G protein-responsive transmembrane adenylyl cyclases (tmAC) or by treatment with cAMP analogues has been shown to either induce or suppress proliferation in different cell types (see, e.g., Hochbaum et al., *J. Biol. Chem.*, 283: 4464-4468 (2008); Misra and Pizzo, *J. Cell. Biochem.*, 108: 998-1011 (2009); Hewer et al., *J. Mol. Cell. Cardiol.*, 50: 87-98 (2011); and Lucchi, et al., *PLoS One*, 6: e20785 (2011)). Similarly, varied effects of cAMP signaling on apoptosis have been reported (see, e.g., Leone et al., *Am. J. Physiol. Gastrointest. Liver Physiol.*, 293: G673-681 (2007); Rudolph et al., *J. Biol. Chem.*, 279: 14828-14834 (2004); Smith et al., *Blood*, 105: 308-316 (2005); and Zhang and Insel, *J. Biol. Chem.*, 279: 20858-20865 (2004)). These discrepancies may be due to differences in cell types or experimental models, or to the lack of specificity regarding tmAC-dependent signals.

The role of sAC-dependent cAMP in the control of cellular proliferation is unknown. Aside from its cytosolic localization, sAC is also present in the nucleus, where it controls the activity of the nuclear cAMP-response-element-binding protein (CREB) transcription factor through protein kinase A (PKA) dependent phosphorylation (see, e.g., Zippin et al., *FASEB J.*, 17: 82-84 (2003)). Recent studies also have demonstrated that sAC migrates from the cytosol to the nucleus when keratinocytes and melanocytes transition from benign cells into cancers, such as squamous cell carcinoma of the skin and melanoma (see, e.g., Zippin, et al., *J. Invest. Dermatol.*, 130: 1279-1287 (2010); and Magro et al., *Arch. Dermatol.*, 148: 335-344 (2012)).

In one embodiment, the invention provides a method of inhibiting proliferation of prostate cancer cells, which comprises contacting prostate cancer cells with a substance that inhibits that activity of a soluble adenylyl cyclase (sAC) protein. The term "prostate cancer," which is also synonymous with the term "prostate carcinoma," refers to cancer that forms in tissues of the prostate. "Prostate cancer cells" refer to cells obtained or derived from a prostate cancer. In another embodiment, the substance that inhibits the activity of the sAC protein can be used to inhibit proliferation of hyperplastic, but not malignant, prostate cells, such as, for example, high grade prostatic intraepithelial neoplasia (HG-PIN) or benign prostatic hyperplasia (BPH), which is also referred to in the art as benign enlargement of the prostate (BEP), adenofibromyomatous hyperplasia, and benign prostatic hypertrophy.

The prostate cancer cells can be of any grade or stage, as determined by histopathology and the Gleason score (discussed below), and/or in accordance with the guidelines described in, e.g., Edge et al. (eds.), *American Joint Committee on Cancer (AJCC) Staging Manual*, 7$^{th}$ Edition (2010), or the SEER Program Coding and Staging Manual, NIH Publication Number 13-5581, U.S. Department of Health and Human Services National Cancer Institute (2013).

The prostate cancer cells can be contacted with any suitable substance that inhibits the activity of a soluble adenylyl cyclase (sAC) protein. Such a substance also is referred to herein as a "sAC inhibitor." For example, the sAC inhibitor can be any andenylyl cyclase inhibitor, many of which are known in the art and are available from commercial sources, such as, for example, Sigma-Aldrich (St. Louis, Mo.). In one embodiment, the substance that inhibits sAC activity is a small molecule. The term "small molecule" refers to a non-biological (i.e., non-protein, nonnucleic acid) substance or compound having a molecular weight of less than about 1,000 g/mol. Small molecule inhibitors of adenylyl cyclases include, for example, cyclopentyladenine monomethanesulfonate (C4479), 2',5'-dideoxyadenosine (D7408), 2',5'-dideoxyadenosine 3'-triphosphate tetrasodium salt (D0939), cis-N-(2-phenylcyclopentyl)-azacyclotridec-1-en-2-amine hydrochloride (MDL-12,330A hydrochloride or M182), 2'/3'-O—(N-methylanthraniloyl)guanosine-5'-(γ-thio) triphosphate triethylammonium salt solution (M6317), and (E)-2-(1H-benzo[d]imidazol-2-ylthio)-N'-(5-bromo-2-hydroxybenzylidene)propanehydrazide (KH7). A preferred small molecule that inhibits the activity of the sAC protein is (E)-2-(1H-benzo[d]imidazol-2-ylthio)-N'-(5-bromo-2-hydroxybenzylidene)propanehydrazide (KH7).

In another embodiment, the substance that inhibits sAC activity is an interfering RNA molecule. RNA interference (RNAi) refers to a biological process in which RNA molecules inhibit gene expression, typically by causing the destruction of specific mRNA molecules. The RNAi molecule can be a small interfering RNA (siRNA), a short hairpin miRNA (shMIR), a microRNA (miRNA), or an antisense nucleic acid. In one embodiment, the sAC inhibitor desirably is a siRNA that specifically targets a gene encoding the sAC protein. RNAi molecules can be generated using any suitable method known in the art (see, e.g., Seyhan et al., *RNA*, 11(5): 837-846 (2005); Huang et al., *Nat. Biotechnol.*, 31(4): 350-356 (2013); Sui et al., *Proc. Natl. Acad. Sci. USA*, 99: 5515-20 (2002); Brummelkamp et al., *Science*, 296: 550-3 (2002); Paul et al., *Nature Biotechnology*, 20: 505-8 (2002); Lee et al., *Nature Biotechnology*, 20: 500-5 (2002); and Castanotto et al., *RNA*, 8: 1454-60 (2002)).

In a preferred embodiment, prostate cancer cells are contacted with the substance that inhibits the activity of the sAC protein by administering the sAC inhibitor directly to a male prostate cancer subject. When the sAC inhibitor is an RNAi molecule, the RNAi molecule can be provided to the male prostate cancer subject using a vector. The vector can be, for example, a plasmid, a cosmid, a viral vector (e.g., retroviral or adenoviral), or a phage. Suitable vectors and methods of vector preparation are well known in the art (see, e.g., Sambrook et al., *Molecular Cloning: A Laboratory Manual*, 4th ed., Cold Spring Harbor Press, Cold Spring Harbor, N.Y. 2012). The sAC inhibitor, or vector encoding the sAC inhibitor, desirably is present in a composition. Preferably, the composition is a pharmaceutically acceptable (e.g., physiologically acceptable) composition, which comprises a carrier, preferably a pharmaceutically acceptable (e.g., physiologically acceptable) carrier, and the sAC inhibitor or vector encoding the sAC inhibitor. Any suitable carrier can be used within the context of the invention, and such carriers are well known in the art. The choice of carrier will be determined, in part, by the particular site to which the composition may be administered and the particular method used to administer the composition. The composition optionally can be sterile. The composition can be frozen or lyophilized for storage and reconstituted in a suitable sterile carrier prior to use. The composition can be generated in accordance with conventional techniques described in, e.g., Remington: *The Science and Practice of Pharmacy*, 21st Edition, Lippincott Williams & Wilkins, Philadelphia, Pa. (2001).

The composition comprising the sAC inhibitor can be administered to a male prostate cancer subject using standard administration techniques, including oral, intravenous, intraperitoneal, subcutaneous, pulmonary, transdermal, intramuscular, intranasal, buccal, sublingual, or suppository administration. The composition preferably is suitable for parenteral administration. The term "parenteral," as used herein, includes intravenous, intramuscular, subcutaneous, rectal, and intraperitoneal administration. More preferably, the composition is administered to a mammal using peripheral systemic delivery by intravenous, intraperitoneal, or subcutaneous injection.

Once administered to a male prostate cancer subject, the sAC inhibitor inhibits proliferation of prostate cancer cells. In this respect, the sAC inhibitor induces a therapeutic effect in the male prostate cancer subject and treats the prostate cancer. As used herein, the terms "treatment," "treating," and the like refer to obtaining a desired pharmacologic and/or physiologic effect. Preferably, the effect is therapeutic, i.e., the effect partially or completely cures a disease and/or adverse symptom attributable to the disease. To this end, the inventive method comprises administering a "therapeutically effective amount" of the substance that inhibits the activity of the sAC protein. A "therapeutically effective amount" refers to an amount effective, at dosages and for periods of time necessary, to achieve a desired therapeutic result. The therapeutically effective amount may vary according to factors such as the disease state, age, and weight of the individual, and the ability of the sAC inhibitor to elicit a desired response in the individual. For example, a therapeutically effective amount of the sAC inhibitor of the invention is an amount which decreases sAC protein bioactivity in a human.

The sAC inhibitor may be administered alone or in combination with other prostate cancer treatments or drugs (e.g., as an adjuvant). In this respect, the sAC inhibitor can be used in combination with, for example, active surveillance, surgery, radiation therapy, hormone therapy, chemotherapy, biologic therapy, bisphosphonate therapy, monoclonal antibody therapy, cryosurgery, high-intensity focused ultrasound, and/or proton beam radiation therapy.

The invention also provides a method for diagnosing prostate cancer in a male subject. The method comprises (a) obtaining a sample of cells from the prostate of a male subject, (b) assaying the sample for expression of the sAC gene or production of the sAC protein, and (c) comparing the level of sAC gene expression or sAC protein production in the sample to a control, wherein overexpression of sAC gene or overproduction of sAC protein in the sample as compared to the control is indicative of prostate cancer in the male subject. The sample of cells desirably is obtained via biopsy, surgical excision (e.g., via radical prostatectomy), or fine needle aspiration (FNA). As used herein, "sample" or "biopsy" refers to a biological specimen removed from a subject for diagnostic analysis. "Fine needle aspiration" refers to a diagnostic procedure used to investigate superficial lumps or masses by inserting a thin, hollow needle is inserted into the mass for sampling of cells. Typically, the sample comprises a biopsy of a prostate region containing or suspected of containing hyperproliferative cells. The sample may be obtained via needle biopsy transrectally or transperineally. Typically, the sample will be formalin-fixed and/or paraffin-embedded for ease of handling.

The presence or absence of sAC gene expression in a cell sample can be determined and evaluated (e.g., assayed) using any suitable method for measuring gene expression. Such methods are known in the art and include, for example, PCR, quantitative RT-PCR, real-time PCR, RNA amplification, in situ hybridization, nucleic acid microarrays, serial analysis of gene expression (SAGE) (Velculescu et al., *Science*, 270: 484-487 (1995)), and Northern blot hybridization.

The presence or absence of sAC protein production in a cell sample can be determined and evaluated (e.g., assayed) using any suitable protein detection method. Such methods are known in the art and include, for example, ELISA, radioimmunoassay (RIA), FACS, immunohistochemistry, immunocytochemistry, and Western blot hybridization. In one embodiment, the sample is assayed for sAC protein expression using immunohistochemistry by staining the sample with an antibody against sAC. The terms "staining" or "immunostaining," as used herein, refer to (i) contacting a sample suspected to contain the sAC protein with an antibody specific for the sAC protein, extracellular or intracellular, under conditions in which a stable antigen-antibody complex can form between the antibody and the protein in the sample, and (ii) detecting any antigen-antibody complex formed in step (i) using any suitable means known in the art, wherein the detection of a complex indicates the presence of sAC protein in the sample.

The antibody directed against sAC (i.e., "anti-sAC antibody") can be any antibody, or antigen-binding fragment thereof, that binds to sAC. The antibody against sAC can be a polyclonal antibody, a monoclonal antibody, a chimeric antibody, a single chain antibody, or a Fab fragment that binds to sAC. For example, the antibody against sAC can be a monoclonal antibody directed against a single sAC epitope, a combination of monoclonal antibodies directed against different epitopes of a single sAC antigenic component, monoclonal antibodies directed towards epitopes of different sAC antigenic components, polyclonal antibodies directed towards the same sAC antigen, or polyclonal antibodies directed towards different sAC antigens.

The antibody can target any epitope of any splice variant of sAC. sAC has several splice variants, including a 48 kDa variant and a 187 kDa variant (see, Buck et al., *Proc. Natl. Acad. Sci. USA*, 96: 79-84 (1999); and Jaiswal et al., *J. Biol. Chem.*, 276: 31698-31708 (2001)). Additional splice variants may also exist. Amino amino acid sequences of full length sAC (sACfl) and truncated sAC (sACt) are disclosed in U.S. Patent Application Publication 2013/0065246. An antibody or antigen-binding fragment thereof directed against sAC can be prepared using any suitable method. For example, a polyclonal antibody can be prepared by immunizing a host animal, e.g., by injection, with the sAC polypeptide or a derivative (e.g., fragment or fusion protein) thereof. A monoclonal antibody can be prepared using hybridoma methodology (see, e.g., Kohler and Milstein, *Nature*, 256: 495-497 (1975)), trioma methodology, human B-cell hybridoma methodology (see, e.g., Kozbor et al., *Immunol. Today*, 4: 72 (1983); and Cote et al., *Proc. Natl. Acad. Sci. USA*, 80: 2026-2030 (1983)), the EBV hybridoma technique (see, .g., Cole et al., "The EBV-hybridoma technique and its application to human lung cancer" in *Monoclonal Antibodies and Cancer Therapy*, Alan R. Liss, Inc., pp. 77-96 (1985)), or by CDR grafting (see, e.g., U.S. Pat. Nos. 5,585,089, 5,693,761, 5,693,762, and 5,225,539). A chimeric antibody can be prepared, for example, by splicing the genes from a mouse antibody specific for the sAC polypeptide together with genes from a human antibody of appropriate biological activity (Morrison et al., *J. Bacteria*, 159: 870 (1984); Neuberger et al., *Nature*, 312: 604-608 (1984); and Takeda et al., *Nature*, 314: 452-454 (1985)). Single chain antibodies can be prepared using methods disclose in, for example, U.S. Pat. Nos. 5,476,786, 5,132, 405, and 4,946,778.

An antibody fragment which binds the sAC protein can be generated in any suitable technique known in the art. Examples of antibody fragments include, but are not limited to, a F(ab')2 fragment, which can be produced by pepsin digestion of the antibody molecule, a Fab' fragment, which can be generated by reducing the disulfide bridges of the F(ab')2 fragment, and a Fab fragment, which can be generated by treating an antibody with papain and a reducing agent.

The antibody against sAC, as bound to sAC present in the sample, is detected so as to obtain or discern the sAC staining pattern. The detection of the antibody against sAC can be accomplished by any suitable technique, including but not limited to enzyme-mediated (e.g., alkaline phosphatase, horseradish peroxidase, etc.) or fluorophore-mediated (e.g., FITC, TRITC, AMCA, etc.) techniques. In one embodiment, antibody binding is detected by detecting a label on the antibody against sAC. In another embodiment, a primary antibody is detected by detecting binding of a secondary antibody or reagent to the primary antibody, wherein, in a further embodiment, the secondary antibody is labeled and detected.

Any suitable label can be utilized so as to obtain or discern the sAC staining pattern. Suitable labels include, but are not limited to, enzyme-based, fluorescent, chemiluminescent, radioactive, and dye molecules. Other reagents and materials can be utilized to obtain or discern the sAC staining pattern, such as dewaxing components to dewax paraffin-embedded samples, pretreatment and blocking reagents, amplification reagents, wash buffers, blocking reagents, and co-staining reagents.

Several anti-sAC antibodies have been identified and include, for example, R5, R6.2, R7, R14, R21, R33, R37, R40, R41, R47.1, R52, R53, R54, and R59 (see, e.g., Kamenetsky, "Mammalian Cells Possess Multiple, Distinctly Regulated cAMP Signaling Cascades," Ph.D. Dissertation, Weill Medical College of Cornell University, Publication No. AAT 3251733 [ProQuest Document ID 1276395511] (2006)). The target sAC epitopes of these antibodies are provided in SEQ ID NOS: 1-8. Preferred antibodies include the R21 antibody, which is a mouse monoclonal antibody directed against amino acids 203-216 of human sACfl protein (Zippin et al., *J. Invest. Dermatol.*, 130(5): 1279-1287 (2010)), the R40 antibody, and the R52 antibody, which binds an epitope comprising SEQ ID NO: 9.

Overexpression of the sAC gene or protein in the sample from the male subject as compared to the control sample is indicative of prostate cancer in the male subject. The sAC gene is "overexpressed" or the sAC protein is "overproduced" when the sAC gene is expressed above normal levels or the sAC protein is produced above normal levels, respectively. Normal expression of the sAC gene or normal production of the sAC protein is the expression of sAC gene or production of the sAC protein, respectively, in a non-diseased subject, or non-diseased tissue from the male subject suspected of having prostate cancer.

Overexpression of the sAC gene or overproduction of the sAC protein can be detected by comparing the level of sAC gene expression or sAC protein production, respectively, in the sample to a control (e.g., a positive or negative control). A control can be provided, for example, by measuring the expression of sAC gene or production of sAC protein in a human subject or sample known to be negative for prostate cancer or a related condition, or in a non-diseased tissue of the male subject suspected of having prostate cancer (negative control), or known to be positive for prostate cancer or a related condition (positive control). The control also can be provided by a previously determined standard prepared by any suitable method (e.g., an expression profile of sAC gene or production profile of sAC protein generated from a population of subjects known to be positive or negative for prostate cancer or a related condition). When comparing the expression of sAC gene or production of sAC protein to a negative control, overexpression or overproduction can be defined as any level of expression or production greater than the level of expression or production, respectively, of the control (e.g., 1.5-fold, 2-fold, 5-fold, 10-fold, 20-fold, 50-fold, 100-fold, or even greater expression as compared to the negative control).

The invention also provides a method for selecting a treatment option for a prostate cancer subject. The method comprises (a) obtaining a sample of prostate cancer cells from a prostate cancer subject, (b) assaying the sample for expression of the sAC gene or production of the sAC protein, (c) comparing the level of sAC gene expression or sAC protein production in the sample to a control, (d) prognosticating the prostate cancer in the subject based on the comparison performed in (c), (e) selecting a treatment option for the subject based on the subject's prognosis in (d), and (f) providing the treatment option to the subject. Descriptions of the prostate cancer cell sample and the assays for sAC gene expression and sAC protein production set forth above in connection with other embodiments of the invention also are applicable to those same aspects of the aforesaid method for selecting a treatment option for a prostate cancer subject.

The term "prognosticate," as used herein, refers to predicting the outcome of a patient's disease state. In the context of the inventive method of selecting a treatment option for a prostate cancer patient, a control can be provided, for example, by measuring the expression of sAC gene or production of sAC protein in a collection of human subjects known to be positive for prostate cancer of various stages. The control also can be provided by a previously determined standard of sAC gene expression or sAC protein production at various prostate cancer stages that is prepared by any suitable method (e.g., an expression profile of sAC gene or production profile of sAC protein generated from a population of subjects known to be positive for different stages of prostate cancer). In this manner, a clinician can compare the prostate cancer subject's sample against multiple different prostate cancer stages to more accurately determine the stage and aggressiveness of the prostate cancer subject's disease.

Prognosticating prostate cancer in the context of the inventive method further comprises calculating the Gleason score for the prostate cancer cell sample. The Gleason score (or Gleason Grading System), is assigned to a prostate cancer based upon its pathology. A higher Gleason score indicates a more aggressive cancer and poorer prognosis. Determining the Gleason score first involves low microscopic examination of a particular prostate cancer sample for specific tumor patterns, which are designated patterns 1-5 and are described in Table 1.

TABLE 1

Patterns for Use in Determining Gleason Score

| Prostate Tumor Pattern | Characteristics |
| --- | --- |
| 1 | cancerous prostate closely resembles normal prostate tissue; glands are small, well-formed, and closely packed; corresponds to a well differentiated carcinoma |

TABLE 1-continued

Patterns for Use in Determining Gleason Score

| Prostate Tumor Pattern | Characteristics |
| --- | --- |
| 2 | tissue still has well-formed glands, but they are larger than the normal glands; corresponds to a well differentiated carcinoma. |
| 3 | tissue still has recognizable glands, but the cells are darker; at high magnification, some of these glands are beginning to invade the surrounding tissue or having an infiltrative pattern; corresponds to a well differentiated carcinoma. |
| 4 | tissue has few recognizable glands; many cells are invading the surrounding tissue in neoplastic clumps; corresponds to a moderately or poorly differentiated carcinoma. |
| 5 | tissue does not have any or only a few recognizable glands; often just sheets of cells throughout the surrounding tissue; corresponds to a poorly differentiated carcinoma |

The Gleason score is calculated as the sum of two numbers: (1) the score of the most common pattern and (2) the score of the second most common pattern. The Gleason Score ranges from 2 to 10, with a score of 10 having the worst prognosis. A Gleason Grade is then assigned based on the Gleason score, which classifies the cancer into a low, intermediate, or high grade. In this respect, a low grade tumor has a Gleason score of 6 or less, an intermediate grade tumor has a Gleason score of 7, and a high grade tumor has a Gleason score of 8-10.

If prognostic tests, such as the Gleason score, indicate that the prostate cancer in the subject may have spread within the prostate or to other parts of the body (i.e., metastasized), additional tests can be performed to determine the exact stage of the cancer so that the most effective treatment option for that stage is selected. Additional tests and procedures that can be performed to accurately stage a prostate cancer include, but are not limited to, bone scans, magnetic resonance imaging (MRI), CAT scan (CT scan), pelvic lymphadenectomy, and seminal vesicle biopsy. The prostate cancer can then be classified as Stage I, Stage II, Stage III, or Stage IV in accordance with the guidelines described in, e.g., Edge et al. (eds.), *American Joint Committee on Cancer (AJCC) Staging Manual*, 7$^{th}$ Edition (2010), or the SEER Program Coding and Staging Manual, NIH Publication Number 13-5581, U.S. Department of Health and Human Services National Cancer Institute (2013).

Once the prognosis of the prostate cancer subject has been determined, the inventive method comprises selecting a treatment option for the subject based on the subject's prognosis and providing the treatment option to the subject. Accurate determination of the stage of prostate cancer in a subject allows for better selection and application of therapeutic methods. Knowledge about the exact stage of prostate cancer affecting a subject allows a clinician to select therapies or treatments that are most appropriate and useful for that subject, while avoiding therapies that are nonproductive or even counterproductive.

The treatment option selected can comprise any suitable therapeutic regimen or pharmaceutical agent known in the art that shows efficacy in treating prostate cancer of any stage, including but not limited to active surveillance, surgery, radiation therapy, hormone therapy, chemotherapy, biologic therapy, bisphosphonate therapy, monoclonal antibody therapy, cryosurgery, high-intensity focused ultrasound, and/or proton beam radiation therapy (see, e.g., Horwich, A., *Ann. Oncol.*, 17 *Suppl.* 10: x211-213 (2006); and Postma R., *Ann. Oncol.*, 17 *Suppl.* 10: x207-210 (2006)). For example, the current standard of care for stage I prostate cancer can include active surveillance, radical prostatectomy (usually with pelvic lymphadenectomy), external-beam radiation therapy, internal radiation therapy, a clinical trial of high-intensity focused ultrasound, and/or a clinical trial of cryosurgery. Standard of care for stage II, III, and IV prostate cancer include many of the treatments employed in stage I prostate cancer, but can further include proton beam radiation therapy, treatments to control the cancer and lessen urinary symptoms (e.g., hormone therapy, internal radiation therapy, transurethral resection of the prostate (TURP), and new types of radiation therapy), and treatments to control pain from cancer that has metastasized to the bone (e.g., pain medication, external-beam radiation, and targeted therapy with a monoclonal antibody).

The following examples further illustrate the invention but, of course, should not be construed as in any way limiting its scope.

Example 1

This example demonstrates that sAC protein is overproduced in prostate cancer cells.

The sAC gene expression, sAC protein subcellular localization, and sAC protein distribution in both benign and malignant prostate tissue samples were examined. Immunohistochemical staining using a mouse monoclonal sAC antibody (R21) was performed on both tumor and benign tissue from 12 radical prostatectomy specimens. Two tumors were well-differentiated (Gleason score 6), 7 were moderately differentiated (Gleason score 7), and 3 were poorly differentiated (Gleason score 8-10).

Briefly, five micron-thick sections of the formalin-fixed paraffin-embedded tissue were deparaffinized and stained using a Bond III Autostainer (Leica Microsystems, Buffalo Grove, Ill.) and the manufacturer's Heat-Induced Epitope Retrieval 1 protocol with supplied reagents. Mouse monoclonal R21 sAC antibody (CEPBiotech, Inc, R21-IHC, Tamarac, Fla.) was used at a dilution of 1:750 as previously described (Zippin, et al., *J. Invest. Dermatol.*, 130: 1279-1287 (2010); and Magro et al., *Arch. Dermatol.*, 148: 335-344 (2012)), followed by treatment in a post primary alkaline phosphatase step for 20 minutes for signal amplification, application of 3,3'-diaminobenzidine for 10 minutes, and finally washing and mounting with a coverslip.

All slides were evaluated in a non-blinded fashion by an experienced urologic pathologist. Test prostate cases were examined by two physicians prior to assessment of the study cases to determine the relative staining intensity categories of weak (1+), moderate (2+), and strong (3+). A histology scoring system (H-score (Barnes et al., *Br. J. Cancer*, 74: 445-51 (1996)), which takes into account the percent of tissue staining for each intensity level, was then used to quantify the amount of staining. The H-score is calculated using the following equation: H-score=(% of cells staining "1+")×1+(% of cells staining "2+")×2+(% of cells staining "3+")×3. Thus, the H-score ranges from 0 to 300. Localization of staining within the cell (i.e., cytoplasmic compartment, apical/luminal border, or nuclear compartment) was recorded for each case. Nuclear staining was positive when sAC-specific DAB precipitate (brown) overlaid and obscured hematoxylin stained (blue) nuclei. Cytoplasmic staining was defined as sAC-specific DAB precipitate not overlaying nuclei. Variations in staining distribution (i.e., tissue near the periphery ("capsule") of the prostate versus more interior regions) were also recorded for each case.

The results of the sAC gene expression/sAC protein production analysis are shown in Table 2. All prostatic glands, whether benign or malignant, showed at least weak (1+) cytoplasmic staining for sAC. When the level of sAC gene expression/sAC protein production was analyzed, prostate cancer glands showed significantly increased sAC staining as compared to benign glands (H-score 189.2 vs. 144.3, respectively; $p<0.01$).

TABLE 2 sAC Gene Expression/sAC Protein Production Analysis Results

| | Benign* | Malignant* | P-values |
|---|---|---|---|
| Expression/Production Level | | | |
| Weak (1+) | 59.6% | 28.3% | 0.022 |
| Moderate (2+) | 36.6% | 54.2% | 0.11 |
| Strong (3+) | 3.8% | 17.5% | 0.028 |
| H-score (mean) | 144.3 | 189.2 | 0.0070 |
| Intensity distribution | | | |
| Increased staining at "capsular" edge | 3/12 | 8/9 | 0.0092 |
| Localization | | | |
| Cytoplasmic | 100% | 100% | 1 |
| Apical/luminal border | 12.4% | 6.8% | 0.063 |
| Nuclear | 7.8% | 2.6% | 0.056 |

*n = 12 for both groups, excepting analysis of "Intensity distribution" for malignant tissue (n = 9)

sAC upregulation was observed at the leading edge of prostate cancer near the prostatic "capsule" and in extraprostatic foci of tumor relative to the center of the tumor, but no significant increase in staining was observed as the tumor invaded deeper into the prostate gland. In contrast, benign glands near the prostatic "capsule" typically did not show any upregulation of sAC when compared to benign glands deeper within the prostate.

Analysis of subcellular distribution of sAC revealed diffuse cytoplasmic staining for sAC in all cells. Some glands also showed more intense staining of nuclei or the apical/luminal border of the cells. Statistical analysis did not reveal any significant difference in the subcellular distribution pattern of sAC between benign prostatic tissue and tumor samples.

The results of this example demonstrate that sAC protein production is elevated in prostate cancer.

Example 2

This example demonstrates that sAC protein is overproduced in prostate cancer cells.

Prostate cancer cases were retrospectively identified from the database of the Division of Surgical Pathology, Weill Cornell Medical College. Tissue microarrays (TMAs) were constructed from the archival formalin-fixed, paraffin-embedded tissue samples using 0.6 mm cores, with each area represented in triplicate. When possible, areas of benign prostatic tissue, high grade prostatic intraepithelial neoplasia (HGPIN), and invasive prostatic adenocarcinoma were all sampled from each case; however, in some cases not all tissue types were present for sampling/evaluation.

Immunohistochemical staining for three sAC antibodies (R21, R40, and R52) was performed on the TMA slides. The TMAs included 50 samples of benign prostatic tissue, 35 samples of HGPIN, 65 samples of localized prostatic adenocarcinoma, and 25 samples of neuroendocrine prostate cancer (NEPC), castration resistant prostate cancer (CRPC), and/or metastatic prostatic adenocarcinoma. Of the 65 localized prostate cancers, 50 were organ-confined (pathologic stage T2), and 15 showed extraprostatic extension and/or seminal vesicle invasion (pathologic stage T3a or T3b). Ten of the localized prostate cancers were well differentiated (Gleason score 6), 50 were moderately differentiated (Gleason score 7), and 5 were poorly differentiated (Gleason score 8-10).

5-μm-thick sections of TMA block containing the formalin-fixed, paraffin-embedded tissue cores were deparaffinized and stained using a BOND-III Autostainer (Leica Microsystems, Buffalo Grove, Ill.) and supplied reagents unless otherwise specified. For the R21 and R52 antibodies, antigen retrieval was performed using the manufacturer's Heat-Induced Epitope Retrieval 1 protocol. For the R40 antibody, no antigen retrieval was performed. Mouse anti-sAC monoclonal antibodies (CEP Biotech, Inc., Tamarac, Fla.) for R21, R40, and R52 were used at dilutions of 1:750, 1:75, and 1:250, respectively, as described previously (Zippin, et al., *J. Invest. Dermatol.*, 130: 1279-1287 (2010); and Magro et al., *Arch. Dermatol.*, 148: 335-344 (2012)). Incubation with the antibodies was followed by treatment in a post-primary alkaline phosphatase step for 20 minutes for signal amplification, application of 3,3'-diaminobenzidine for 10 minutes, and finally washing and mounting with a coverslip.

All slides were evaluated in a semi-blinded fashion by an experienced urologic pathologist. Test prostate cases were examined by two physicians prior to assessment of the study cases to determine the relative staining intensity categories of weak (1+), moderate (2+), and strong (3+). The H-score (Barnes et al., supra) was calculated as described in Example 1 and used to quantify the amount of staining Localization of the staining within the cell (cytoplasmic compartment, apical/luminal border, or nuclear compartment) was recorded for each case. Nuclear staining was positive when the sAC-specific diaminobenzidine precipitate (brown) overlaid and obscured hematoxylin-stained (blue) nuclei. In some cases, only the nucleoli showed reactivity. Cytoplasmic staining was defined as sAC-specific diaminobenzidine precipitate not overlaying nuclei. For the R40 antibody, the percentage of positive nuclear staining (including those with only nucleolar staining) was also recorded. The results of sAC staining with R21, R40, and R52 antibodies are shown in Tables 3, 4, and 5, respectively.

TABLE 3

R21 Immunohistochemical Analysis of sAC Expression/Production

| | H-score (mean) |
|---|---|
| Benign/Malignant | |
| Benign | 135.2 |
| HGPIN | 152.9 |
| Malignant | 192.1 |
| Within Tumor Groups | |
| pT2 | 172.1 |
| pT3 | 210.4 |
| Gleason 6 | 152.7 |
| Gleason 7 | 171.9 |
| Gleason 8-10 | 195.0 |

TABLE 3-continued

R21 Immunohistochemical Analysis of sAC Expression/Production

| | H-score (mean) |
|---|---|
| Metastatic Prostate Cancer | |
| Benign | 135.2 |
| Localized Prostate Cancer | 192.1 |
| Met/CRPC/NEPC | 185.6 |

R21 staining was invariably cytoplasmic with occasional accentuation of luminal border and/or nuclear staining Malignant tumors showed significantly stronger staining as compared to benign prostatic tissue. High grade prostatic intraepithelial neoplasia (HGPIN), a proposed precursor to cancer and/or marker of cancer risk, showed increased staining over benign prostatic tissue but less staining than invasive carcinoma. Within the tumor groups, higher grade and higher stage tumors had a higher H-score (i.e., more likely to have 3+ staining) Metastatic prostate cancers, castration resistant prostate cancers (CRPC), and neuroendocrine prostate cancers (NEPC) exhibited variable staining that was not definitively increased over localized prostate cancer, but was greater than benign prostatic tissue.

TABLE 4

R40 Immunohistochemical Analysis of sAC Expression/Production

| | H-score (mean) |
|---|---|
| Benign/Malignant | |
| Benign | 53.6 |
| HGPIN | 64.2 |
| Malignant | 82.8 |
| Within Tumor Groups | |
| pT2 | 81.1 |
| pT3 | 83.7 |
| Gleason 6 | 80.9 |
| Gleason 7 | 84.5 |
| Gleason 8-10 | 79.2 |
| Metastatic Prostate Cancer | |
| Benign | 53.6 |
| Localized Prostate Cancer | 82.8 |
| Met/CRPC/NEPC | 50.4 |

R40 staining was cytoplasmic and rarely 3+ in intensity, with most cases (benign or malignant) showing 0 or 1+ staining No appreciable luminal accentuation and/or nuclear positivity was observed. Within the tumor groups, higher grade and higher stage tumors had similar H-scores. Metastatic prostate cancers, castration resistant prostate cancers (CRPC), and neuroendocrine prostate cancers (NEPC) showed decreased expression/production of R40 as compared to the increased frequency of negative (0+) staining in localized prostate cancer.

TABLE 5

R52 Immunohistochemical Analysis of sAC Expression/Production

| | H-score (mean) | Mean % positive nuclei |
|---|---|---|
| Benign/Malignant | | |
| Benign | 42.0 | 1.3 |
| HGPIN | 45.7 | 2.2 |
| Malignant | 62.7 | 5.9 |

TABLE 5-continued

R52 Immunohistochemical Analysis of sAC Expression/Production

|  | H-score (mean) | Mean % positive nuclei |
|---|---|---|
| Within Tumor Groups | | |
| pT2 | 60.8 | 3.4 |
| pT3 | 68.2 | 7.5 |
| Gleason 6 | 50.1 | 2.3 |
| Gleason 7 | 59.9 | 3.6 |
| Gleason 8-10 | 69.1 | 8.9 |
| Metastatic Prostate Cancer | | |
| Benign | 42.0 | 1.3 |
| Localized Prostate Cancer | 62.7 | 5.9 |
| Met/CRPC/NEPC | 72.4 | 13.6 |

R52 staining was predominantly cytoplasmic and generally absent or weak (i.e., 0 or 1+ staining with occasional 2+ and rarely 3+ staining) Malignant tumors showed a slight increase in cytoplasmic staining over benign prostatic tissue. Staining with the R52 antibody revealed rare positive nuclei in benign cells and an increased percentage of sAC-positive nuclei, including some nucleolar positivity, in malignant tumors. Within the tumor groups, higher grade and higher stage tumors exhibited similar cytoplasmic H-scores but a higher percentage of sAC-positive nuclei (including nucleolar positivity). Metastatic prostate cancers, castration resistant prostate cancers (CRPC), and neuroendocrine prostate cancers (NEPC) showed an increased percentage of sAC-positive nuclei (including nucleolar positivity) compared to localized prostate cancer.

The results of this example demonstrate that sAC protein production is elevated in prostate cancer.

Example 3

This example demonstrates a method of inhibiting proliferation of prostate cancer cells by suppressing the activity of soluble adenylyl cyclase (sAC) protein.

The androgen-sensitive LNCaP (ATCC-Nr. CRL-1740D) human prostate carcinoma cell line, the androgen-insensitive PC3 (ATCC-Nr. CRL-1435D) human prostate carcinoma cell line, and neuroblastoma cell line SH-SY5Y (ATCC-Nr. CRL-2266) were purchased from the American Type Culture Collection, and human normal prostate epithelial cell line PNT2 was purchased from Sigma-Aldrich (Cat. Nr. 95012613). Cells were expanded and frozen in aliquots within four weeks of purchase. Cells were thawed and cultured for no more than three further passages. PNT2 cells were cultured in medium RPMI1640 supplemented with 10% fetal calf serum, glutamine and antibiotics. All other cells were cultured in Dulbecco's modified Eagle's medium that was supplemented with 5% fetal calf serum, glutamine, and antibiotics. The cells ($1.5 \times 10^5$) were seeded in culture medium with 2% fetal calf serum 24 hours prior to each experiment.

Production of sAC protein in the LNCaP and PC3 prostate carcinoma cell lines was analyzed by Western blot. In particular, cells were lysed in Laemmli buffer containing 2% SDS, 10% glycerol, 5% 2-mercaptoethanol, 0.002% bromphenol blue, and 0.0625 mol/liter Tris-HCl. Equal amounts of total proteins were separated on SDS-polyacrylamide gels and transferred to a nitrocellulose membrane. The following primary antibodies were used: sAC (clones R21 and R40; provided by Dr. J. Buck) and actin (Millipore, Billerica, Mass.). After incubation with peroxidase-linked and horseradish peroxidase-labeled secondary antibodies, specific bands were visualized by chemiluminescence using an ECL Plus kit. Equivalent sample loading was confirmed by stripping the membranes with RESTORE™ Western blot stripping buffer (Thermo Fisher Scientific, Rockford, Ill.), followed by treatment with anti-actin antibody.

Figure 1:
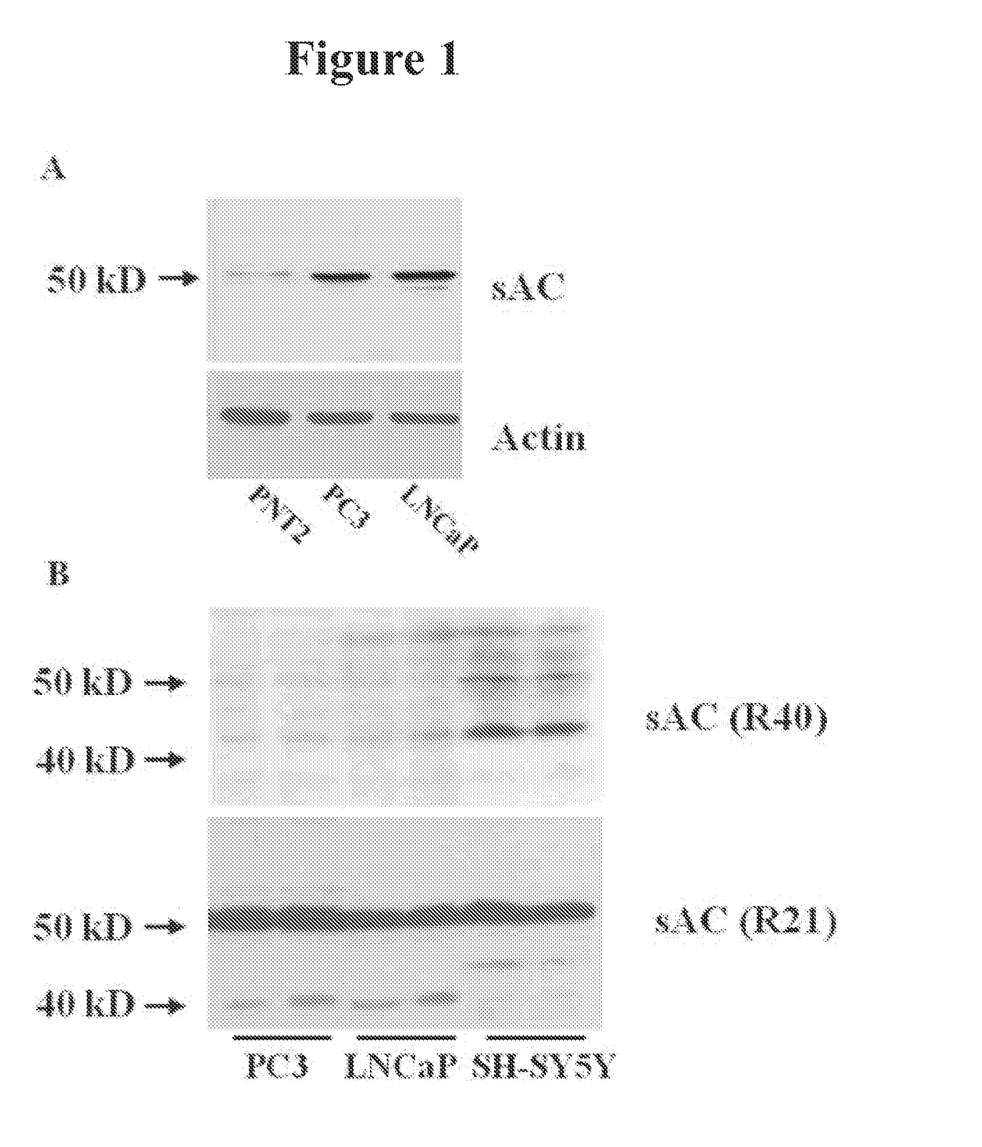
FIG. 1A is an image depicting data from Western blot analysis of sAC expression performed with lysates of the following untreated cell lines: PNT2, PC3 and LNCaP.
FIG. 1B is an image depicting data from sAC isoform-specific Western blot analysis in PC3 and LNCaP cell lines using the R40 antibody (recognizing only the "testicular" sAC isoform) and the R21 antibody (recognizing the sAC "testicular and "somatic" isoforms).

The LNCaP and PC3 prostate carcinoma cell lines exhibited increased production of sAC as compared to normal human PNT2 prostate epithelial cells, as shown in FIG. 1A. Furthermore, analyzing isoform-specific expression by using the R40 antibody, which recognize only the "testicular" isoform, and the R21 antibody, which recognizes both the "testicular and "somatic" isoforms (see Farrell et al., *PLoS ONE*, 22: e3251 (2008)), revealed weak expression of the "testicular" isoform in both cell lines, as shown in FIG. 1B, suggesting that the "somatic" isoform is a predominant form of sAC in these cells.

Treatment of PC3 and LNCaP cells with the selective sAC inhibitor KH7 was used to suppress the activity of sAC. Previous studies demonstrated that KH7 inhibits sAC in various cell types at a concentration range of 10-30 µmol/L, but has no effect on tmAC and soluble guanylyl cyclase up to 100 µmol/L (Hess et al., *Dev. Cell.*, 9: 249-259 (2005)). To further discriminate against possible nonspecific sAC-independent effects of KH7, an inactive analogue of KH7, KH7.15 (Wu et al., *Nat. Neurosci.*, 9: 1257-1264 (2006)), was used.

Figure 2:
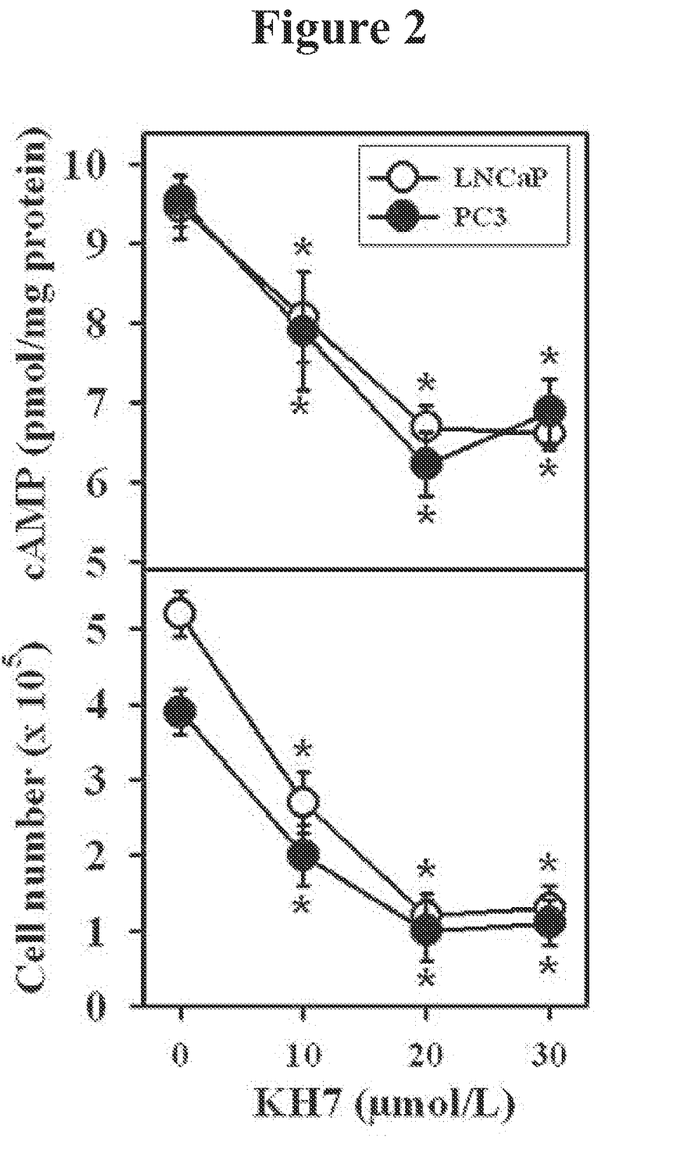
FIG. 2 is a graph which illustrates experimental data depicting the effects of the sAC inhibitor KH7 on prostate cancer cell proliferation. Statistical analyses are presented for cellular cAMP content and cell number per dish (starting density: 150,000 cells/dish) 24 hours after KH7 treatment. Values are the mean±SEM (n=5-8). *p<0.05 vs. 0 μmol/L KH7.

Treatment with KH7 reduced the intracellular cAMP content and suppressed cell proliferation in a dose-dependent manner in both cell lines with a maximal effect at 20 µmol/L, as shown in FIG. 2. Analysis of cell growth and death following treatment with 20 µmol/L KH7 for 48 hours revealed that the anti-proliferative effect of sAC inhibition was accompanied by the release of LDH and apoptosis, as measured by a rise in the subG1 population and cleavage of caspase-3. In contrast, treatment with the inactive analogue KH7.15 had no effect, suggesting that the observed effects of KH7 treatment were sAC-dependent.

To further substantiate the role of sAC in cell growth and death, the sAC gene expression/sAC protein production was suppressed in LNCaP cells. Two different methods of sAC knockdown, lipofectamine-based transfection with sAC-specific siRNA or adenoviral transfection with shRNA, were used to further rule out the possibility of KH7 off-target effects. For lipofectamine-based siRNA transfection, LNCaP cells were treated with siRNA duplexes that consisted of four different predesigned sequences targeting the human sAC mRNA sequence (GenBank Accession No. NM_001167749; Dharmacon, Lafayette, Colo.; catalogue no. L-006353-00,). In the control group, cells were treated with scrambled non-targeting siRNA (Dharmacon, Lafayette, Colo.; catalogue no. D-001810-10). Cells were transfected following the manufacturer's instructions. Briefly, cells were seeded 1 day before transfection in Dulbecco's modified Eagle's medium that was supplemented with 2% fetal calf serum without antibiotics. Targeting or non-targeting siRNA was mixed with Lipofectamine 2000 (Life Technologies, Carlsbad, Calif.) in Opti-MEM medium (Life Technologies, Carlsbad, Calif.) for 20 minutes at room temperature and then added to the cell culture medium at a final concentration of 40 nmol/liter. The cells were incubated at 37° C. for 6 hours, and the medium was changed to normal growth medium (1% fetal calf serum) for an additional 42 hours. The concentration of fetal calf serum was then increased to 2%, and the cells were cultured for an additional 24 hours.

The experimental procedure and methodology for sAC knockdown in LNCaP cells using adenovirus-driven transcription with shRNA were adapted from a previously described protocol (Rinne et al., *J. Muscle Res. Cell. Motil.*, 27: 413-421 (2006)). In particular, the shRNA adenovirus vectors were constructed using the AdEasy adenoviral vector system. The pAd-Track-CMV shuttle vector was used to insert the murine U6 promoter and the anti-sAC-directed shRNA sequence as a double-stranded oligonucleotide using the BglII and KpnI restriction sites. The pmU6pro vector, which contains the murine U6 snRNA promoter, served as a template. To produce shRNA-encoding vectors, the U6 promoter and the hairpin construct were fused using a universal U6 5-primer and a 3-primer that included the siRNA targeting the rat sAC mRNA sequence (GenBank Accession No. NM_021684.1; boldface) and complementary U6 promoter sequences (italic):

(SEQ ID NO: 10)
5-GGGGTACCAAAAAAGTGGAAAGTGGAACGAAAGCATCTCTTGAA

TGCTTTCGTTCCACTTTCCAC*AAACAAGGCTTTTCTCCAAG*-3.

The underlined sequence corresponds to the hairpin loop. This sequence was effective in inhibiting human sAC expression/sAC protein production even though homology is not 100%. A randomized sequence (scrambled) that was based on SEQ ID NO: 9 served as a control. Recombinant adenovirus plasmids were generated by homologous recombination between pAd-Track-sh-sAC and pAd-Easy1 in *E. coli* to produce the recombinant viruses. The recombinant viruses were propagated in HEK293 cells and recovered after several freeze-thaw cycles. The cells were infected using $10^6$ viral particles/mL of culture medium.

Figure 3:
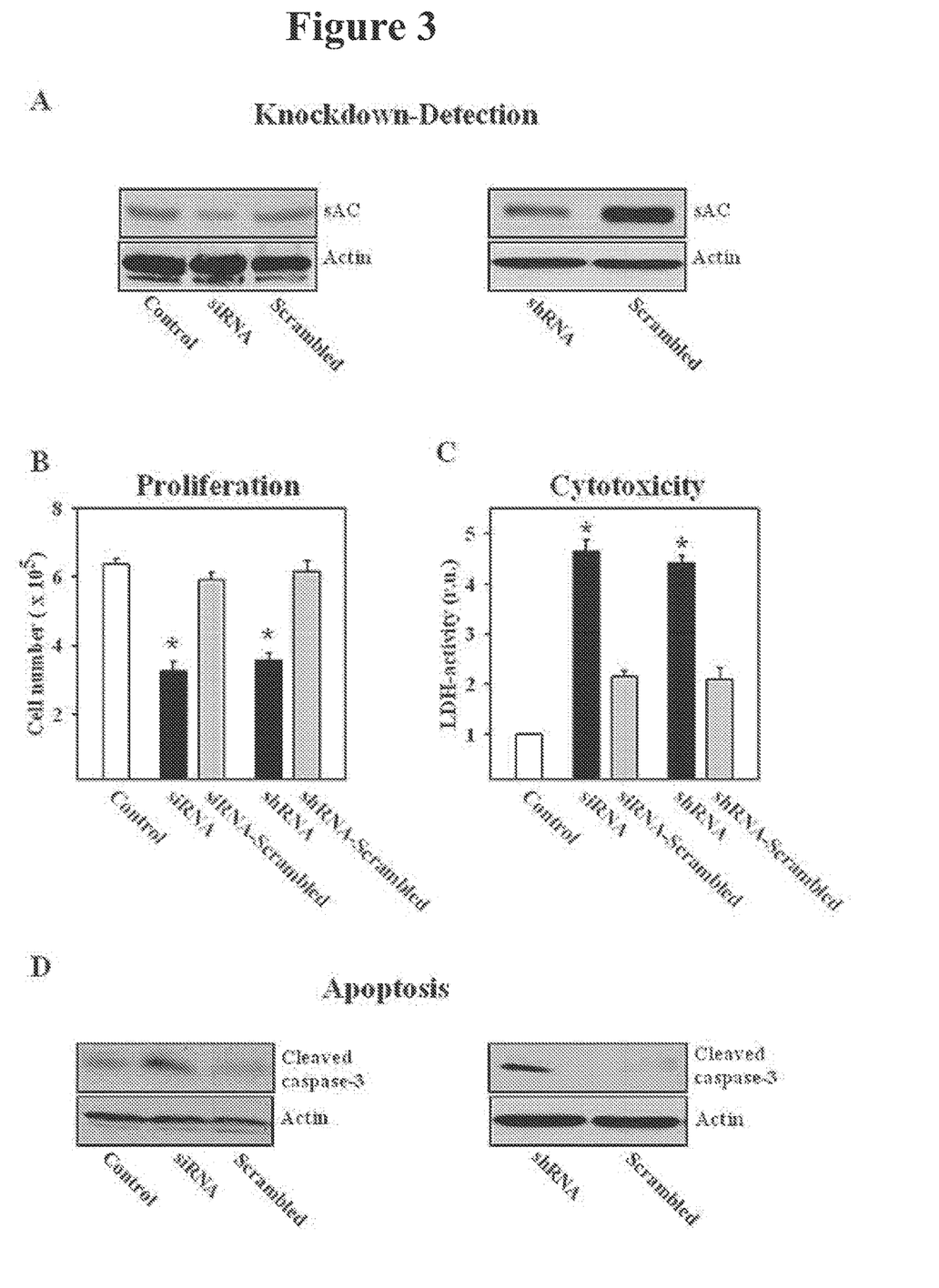
FIG. 3A is an image depicting data from Western blot analysis of lysates of LNCaP cells after treatment with sAC-specific or scrambled siRNA for 72 hours (left panel) or after treatment with sAC-specific or scrambled shRNA for 72 hours (right panel).
FIGS. 3B-D are graphs and images which illustrate experimental data depicting the effects of siRNA or shRNA transfection on cell proliferation (FIG. 3B), LDH activity in the cell culture medium (relative units (r.u.)) (FIG. 3C), and cleavage of caspase-3 (FIG. 3D). Values are the mean±S.E. (n=5-6), *:p<0.05 versus control or scrambled. The Western blot data are representative of five independent experiments with similar results.

Both knockdown methods equally reduced the expression of the 50 kDa sAC isoform by ≥80%, as shown in FIG. 3A. Similar to pharmacological inhibition of sAC with KH7, both methods of sAC knockdown significantly suppressed the proliferation of LNCaP cells (reduction of cell numbers from $6.37 \times 10^5$ to $3.25 \times 10^5$ under siRNA treatment and to $3.56 \times 10^5$ under shRNA treatment), induced LDH release, and led to caspase-3 cleavage, as shown in FIGS. 3B-3D. In contrast, treatment with scrambled siRNA or shRNA had no effect on these parameters.

These results demonstrate a method of inhibiting proliferation of prostate cancer cells by inhibiting sAC gene expression/sAC protein production.

Example 4

This example demonstrates that inhibition of sAC expression/sAC protein production leads to cell cycle arrest.

To understand the mechanisms responsible for the antiproliferative effect of sAC inhibition, cell cycle analysis was performed using FACS-based cell cycle analysis. Specifically, LNCaP cells were fixed with 70% alcohol, stained with propidium iodide, and treated with RNase (BD Biosciences, San Jose, Calif.). DNA content was analyzed using a FACSCALIBUR™ flow cytometer (BD Biosciences, San Jose, Calif.) and FLOWJO™ software.

Figure 4:
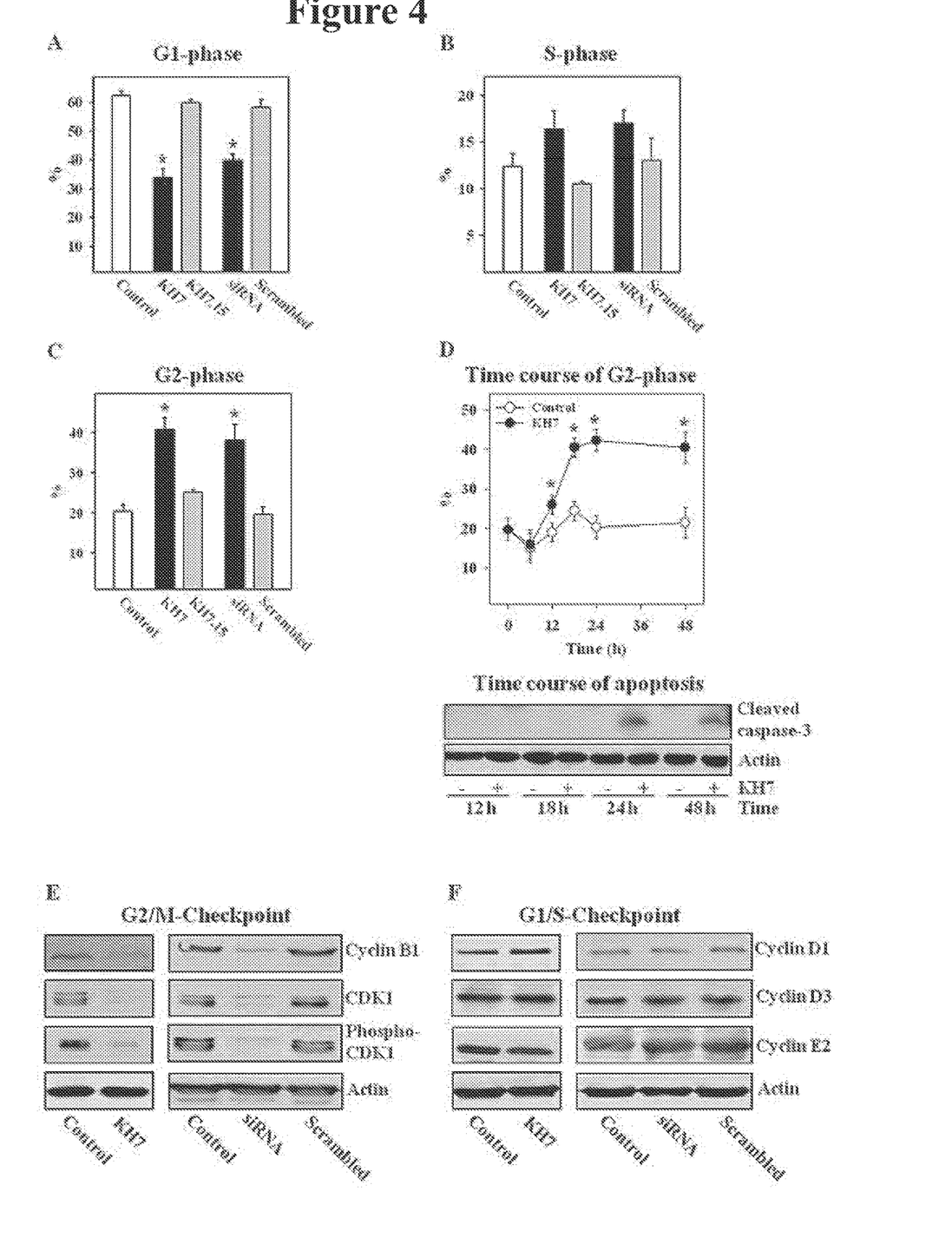
FIGS. 4A-4C are graphs depicting statistical analysis of cell cycle phases carried out by flow cytometry with control LNCaP cells, with cells treated either with the sAC inhibitor KH7 (20 mol/liter) or with the inactive analog KH7.15 (20 mol/liter) for 24 hours, or with cells transfected with sAC-specific or scrambled siRNA.
FIG. 4D includes a graph and image showing the time course for the $G_2$ phase population and caspase-3 cleavage, respectively, as examined in LNCaP cells treated for 48 hours with the sAC inhibitor KH7. Values are the mean±S.E. (n=8-10), *:p<0.05 versus control or scrambled siRNA.
FIGS. 4E and 4F are images depicting Western blot analysis of proteins controlling cell cycle progression through the G2/M and G1/S checkpoints performed with lysates of control LNCaP cells or cells treated with KH7 for 24 hours or after sAC knockdown (siRNA). Treatment conditions were similar to those described for FIGS. 4A-4D. All Western blot data are representative of three to five independent experiments with similar results.

In LNCaP cells, pharmacologic or genetic suppression of sAC activity significantly increased the percentage of cells in G2-phase and subsequently reduced the percentage of cells in G1-phase, suggesting the development of cell cycle arrest at the G2/M checkpoint, as shown in FIGS. 4A-4C. Further kinetic analysis of cell cycle arrest progression revealed that the percentage of cells in G2-phase started to rise 12 hours after treatment with the sAC inhibitor and reached a maximal value at 24 hours, as shown in FIG. 4D. In contrast, cleavage of caspase-3 first appeared after 24 hours. Therefore, apoptosis appears to be a result, rather than a cause, of the cell cycle arrest.

To investigate how sAC controls the G2/M transition, the expression of various cyclins and CDK1 was examined via Western blot as described above using the following primary antibodies: CDK1, phospho-CDK1, cyclin B1, cyclin D1, cyclin D3, and cyclin E2. Expression of cyclin B1 and CDK1 (both the phosphorylated and dephosphorylated forms) were significantly suppressed by treatment with KH7, as evidenced by a reduction of optical band density expressed as a ratio to actin band density by 66% (cyclin B1), 64% (CDK1) and 78% (phospho-CDK1) from control levels. Similar effects were found after sAC knockdown: reduction by 70% (cyclin B1), 75% (CDK1) and 78% (phospho-CDK1) from control levels, as shown in FIG. 4E. In contrast, expression of cyclin D1, cyclin D3, and cyclin E2, the proteins responsible for the G1/S transition, were not altered by sAC inhibition, as shown in FIG. 4F. Therefore, these data support the specific role of sAC in controlling the G2/M transition.

Figure 5:
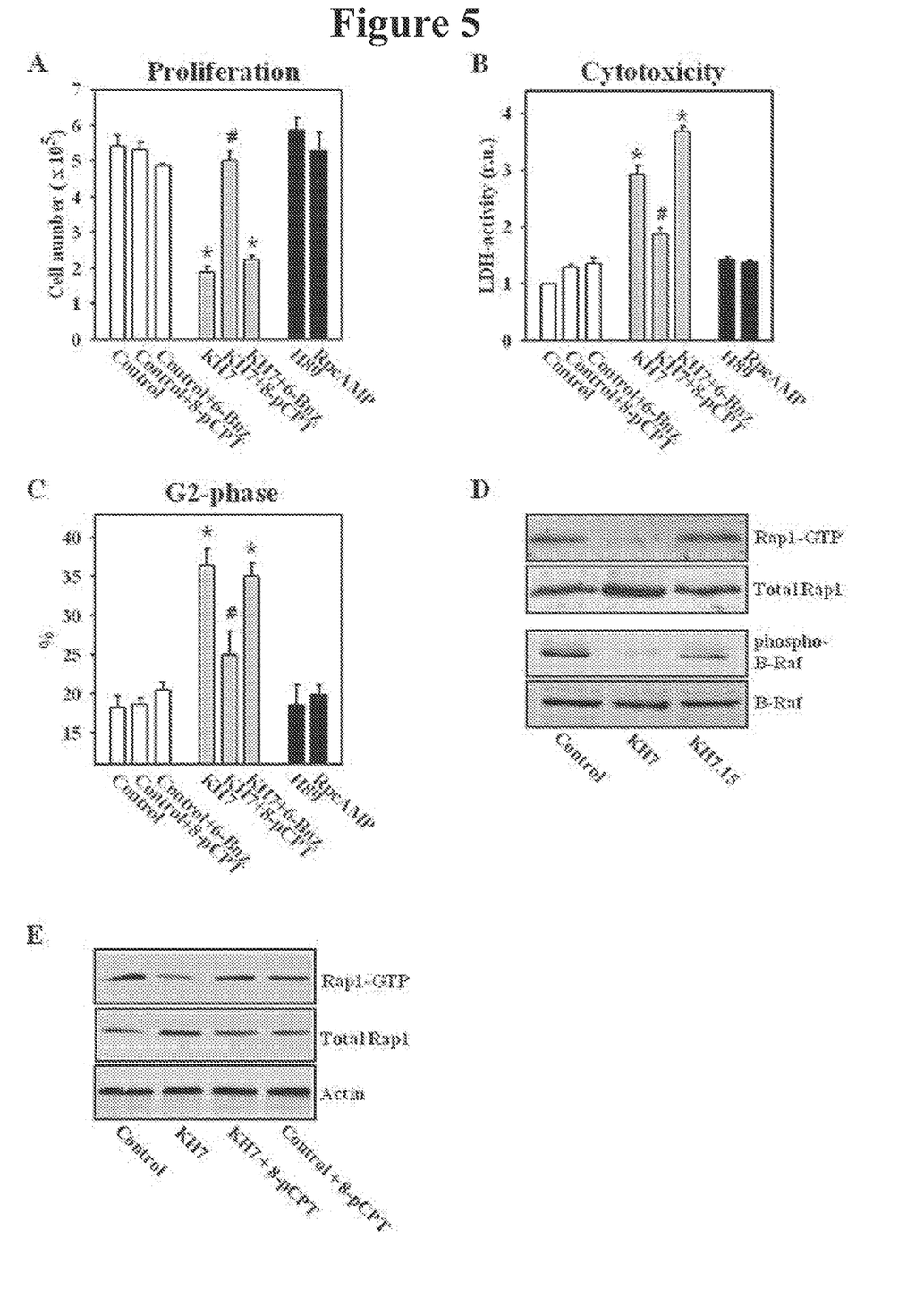
FIGS. 5A-5C are graphs depicting statistical analyses of cell number per dish (FIG. 5A), LDH activity in the cell culture medium (relative units (r.u.)) (FIG. 5B), and G2 phase populations (FIG. 5C). Treatments (all 24 hours) were as follows: 20 mol/liter KH7, 20 mol/liter KH7.15, 100 mol/liter 8-pCPT-cAMP (8-pCPT), 100 mol/liter N6-benzoyl-cAMP (6-Bnz), 3 mol/liter H-89, or 100 mol/liter (Rp)-cAMP-S(RpcAMP). Values are the mean±S.E. (n=8-11), *:p<0.05 versus the control; #:p<0.05 versus KH7.
FIGS. 5D and 5E are images depicting Western blot analysis of the active form of Rap1 (Rap1-GTP) and phosphorylated forms of B-Raf performed with LNCaP cell lysates. Treatment conditions were similar to those described for FIGS. 5A-5C. Treatment was performed for 18 hours. All Western blot data are representative of four to six independent experiments with similar results.

PKA and exchange protein activated by cAMP (EPAC) are two major downstream targets of cAMP. Therefore, the potential role of these proteins in sAC-dependent proliferation control was investigated. The role of PKA was investigated first by applying the PKA-specific activator $N^6$-benzoyl-cAMP. Treatment with this compound had no effect on proliferation in control cells or in cells treated with the sAC inhibitor KH7, as shown in FIGS. 5A-5C. Cells also were treated with two structurally different PKA inhibitors, the ATP-binding site inhibitor H-89 (3 μmol/L) and the cAMP-binding site inhibitor RpcAMP (100 μmol/L). Treatment with these inhibitors had no effect on the proliferation, cytotoxicity or distribution of the cell population within the cell cycle, as shown in FIGS. 5A-5C.

To test the role of EPAC in proliferation control, the effects of inhibition of sAC on EPAC activity in LNCaP cells was examined. To trace the EPAC activity, the expression of an active form of Rap1, GTP-bound Rap1, was analyzed by Western blot as described above using an anti-Rap1A primary antibody (Jena Bioscience, Jena, Germany). sAC inhibition with KH7 significantly depleted Rap1-GTP, whereas treatment with its inactive analogue, KH7.15, had no effect, as shown in FIG. 5D. Similarly, inhibition of sAC suppressed the phosphorylation of B-Raf, a downstream kinase activated by Rap1, as demonstrated via Western blot using phospho-B-Raf, and B-Raf primary antibodies (Cell Signaling, Frankfurt, Germany). Analyzing optical band density expressed as a ratio to actin band density did not reveal any significant effect of KH7 treatment on expression of Rap1 (0.81+0.07 vs. 0.79+0.01 in control, n=6) or B-Raf (1.02+0.04 vs. 1.13+0.06 in control, n=8).

Treatment with a selective EPAC activator, 8-pCPT, reversed the effect of KH7 on Rap1-GTP expression, as shown in FIG. 5E. Further analysis revealed that treatment with the EPAC activator prevented the decrease in cell proliferation, LDH release, and the cell cycle block induced by sAC inhibition.

These results evidence that sAC controls the cell cycle and proliferation in an EPAC/Rap1-dependent, PKA-independent manner.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of inhibiting proliferation of prostate cancer cells, which method comprises,
   (a) obtaining a sample of cells from the prostate of a male subject,
   (b) assaying the sample for nuclear expression of the soluble adenylyl cyclase (sAC) protein,
   (c) determining the percentage of sAC protein positive nuclei in the sample,
   (d) comparing the percentage of sAC protein positive nuclei in the sample to the percentage of sAC protein positive nuclei in a control sample, and
   (e) administering a sAC inhibitor to the subject determined to have an increased percentage of sAC protein positive nuclei compared to the control sample, whereupon proliferation of the prostate cancer cells is inhibited.

2. The method of claim 1, wherein the sAC inhibitor is a small molecule that inhibits sAC protein activity in the prostate cancer cell.

3. The method of claim 2, wherein the small molecule is (E)-2-(1H-Benzo[d]imidazol-2-ylthio)-N'-(5-bromo-2-hydroxybenzylidene)propanehydrazide (KH7).

4. The method of claim 1, wherein the sample of cells is obtained via biopsy, tissue excision, or fine needle aspiration (FNA).

5. The method of claim 1, wherein the method further comprises treatment of the subject with surgery, radiation therapy, hormone therapy, chemotherapy, biologic therapy, bisphosphonate therapy, monoclonal antibody therapy, cryosurgery, high-intensity focused ultrasound, proton beam radiation therapy, or any combination of the foregoing treatment options.

6. The method of claim 1, wherein nuclear expression of the sAC protein is determined with an anti-sAC antibody that binds to an epitope comprising the amino acid sequence of SEQ ID NO: 9.

* * * * *

SEQUENCE LISTING

```
<160> NUMBER OF SEQ ID NOS: 10

<210> SEQ ID NO 1
<211> LENGTH: 50
<212> TYPE: PRT
<213> ORGANISM: Homo sapiens
<220> FEATURE:
<221> NAME/KEY: MISC_FEATURE
<223> OTHER INFORMATION: peptide sequence containing the epitopes
      of anti-sAC antibodies R40 and R33

<400> SEQUENCE: 1

Met Phe Val Asp Ile Ser Gly Phe Thr Ala Met Thr Glu Lys Phe Ser
1               5                   10                  15

Ser Ala Met Tyr Met Asp Arg Gly Ala Glu Gln Leu Val Glu Ile Leu
            20                  25                  30

Asn Tyr His Ile Ser Ala Ile Val Glu Lys Val Leu Ile Phe Gly Gly
        35                  40                  45

Asp Ile
    50

<210> SEQ ID NO 2
<211> LENGTH: 50
<212> TYPE: PRT
<213> ORGANISM: Homo sapiens
<220> FEATURE:
<221> NAME/KEY: MISC_FEATURE
<223> OTHER INFORMATION: peptide sequence containing the epitopes
      of anti-sAC antibodies R7, R21, and R53

<400> SEQUENCE: 2

Asp Asp Val Arg Leu Ala Gln Asn Met Ala Gln Met Asn Asp Val Ile
1               5                   10                  15

Leu Ser Pro Asn Cys Trp Gln Leu Cys Asp Arg Ser Met Ile Glu Ile
            20                  25                  30

Glu Ser Val Pro Asp Gln Arg Ala Val Lys Val Asn Phe Leu Lys Pro
        35                  40                  45

Pro Pro
    50
```

<210> SEQ ID NO 3
<211> LENGTH: 42
<212> TYPE: PRT
<213> ORGANISM: Homo sapiens
<220> FEATURE:
<221> NAME/KEY: MISC_FEATURE
<223> OTHER INFORMATION: peptide sequence containing the epitopes
      of anti-sAC antibodies R5, R6.2, R14, R37,
      R41, R47.1, R52, R54, and R59

<400> SEQUENCE: 3

Ser Val Thr Tyr Asn Gly Ser Asn Leu Pro Ala Tyr Phe Phe Lys Glu
1               5                   10                  15

Leu Pro Lys Lys Val Met Lys Gly Val Ala Asp Ser Gly Pro Leu Tyr
                20                  25                  30

Gln Tyr Trp Gly Arg Thr Glu Lys Val Met
            35                  40

<210> SEQ ID NO 4
<211> LENGTH: 16
<212> TYPE: PRT
<213> ORGANISM: Homo sapiens
<220> FEATURE:
<221> NAME/KEY: MISC_FEATURE
<223> OTHER INFORMATION: peptide sequence containing the epitope
      of antibody R33

<400> SEQUENCE: 4

Ala Met Tyr Met Asp Arg Gly Ala Glu Gln Leu Val Glu Ile Leu Asn
1               5                   10                  15

<210> SEQ ID NO 5
<211> LENGTH: 14
<212> TYPE: PRT
<213> ORGANISM: Homo sapiens
<220> FEATURE:
<221> NAME/KEY: MISC_FEATURE
<223> OTHER INFORMATION: peptide sequence containing the epitopes
      of anti-sAC antibodies R7, R21, and R53

<400> SEQUENCE: 5

Glu Ile Glu Ser Val Pro Asp Gln Arg Ala Val Lys Val Asn
1               5                   10

<210> SEQ ID NO 6
<211> LENGTH: 15
<212> TYPE: PRT
<213> ORGANISM: Homo sapiens
<220> FEATURE:
<221> NAME/KEY: MISC_FEATURE
<223> OTHER INFORMATION: peptide sequence containing the epitope
      of antibody R37

<400> SEQUENCE: 6

Glu Leu Pro Lys Lys Val Met Lys Gly Val Ala Asp Ser Gly Pro
1               5                   10                  15

<210> SEQ ID NO 7
<211> LENGTH: 16
<212> TYPE: PRT
<213> ORGANISM: Homo sapiens
<220> FEATURE:
<221> NAME/KEY: MISC_FEATURE
<223> OTHER INFORMATION: peptide sequence containing the epitopes
      of anti-sAC antibodies R5 and R37

<400> SEQUENCE: 7

-continued

```
Asn Leu Pro Ala Tyr Phe Phe Lys Glu Leu Pro Lys Lys Val Met Lys
1               5                   10                  15

<210> SEQ ID NO 8
<211> LENGTH: 17
<212> TYPE: PRT
<213> ORGANISM: Homo sapiens
<220> FEATURE:
<221> NAME/KEY: MISC_FEATURE
<223> OTHER INFORMATION: peptide sequence containing the epitopes
      of anti-sAC antibodies R6.2, R14, R37,
      R41, R41.7, R52, R54, and R59

<400> SEQUENCE: 8

Met Lys Gly Val Ala Asp Ser Gly Pro Leu Tyr Gln Tyr Trp Gly Arg
1               5                   10                  15

Thr

<210> SEQ ID NO 9
<211> LENGTH: 17
<212> TYPE: PRT
<213> ORGANISM: Homo sapiens

<400> SEQUENCE: 9

Met Lys Gly Val Ala Asp Ser Gly Pro Leu Tyr Gln Tyr Trp Gly Arg
1               5                   10                  15

Thr

<210> SEQ ID NO 10
<211> LENGTH: 85
<212> TYPE: DNA
<213> ORGANISM: Artificial Sequence
<220> FEATURE:
<223> OTHER INFORMATION: Synthetic

<400> SEQUENCE: 10
ggggtaccaa aaaagtggaa agtggaacga aagcatctct tgaatgcttt cgttccactt      60
tccacaaaca aggcttttct ccaag                                           85
```